United States Patent
Beesley et al.

(10) Patent No.: US 9,976,644 B2
(45) Date of Patent: May 22, 2018

(54) DIFFERENTIAL CARRIER TEMPERATURE SENSING METHOD

(71) Applicant: Dana Automotive Systems Group, LLC, Maumee, OH (US)

(72) Inventors: Peter A. Beesley, Fort Wayne, IN (US); Perry M. Paielli, Commerce Township, MI (US)

(73) Assignee: Dana Automotive Systems Group, LLC, Maumee, OH (US)

( * ) Notice: Subject to any disclaimer, the term of this patent is extended or adjusted under 35 U.S.C. 154(b) by 0 days. days.

(21) Appl. No.: 15/478,497

(22) Filed: Apr. 4, 2017

(65) Prior Publication Data
US 2017/0204959 A1 Jul. 20, 2017

Related U.S. Application Data

(62) Division of application No. 14/197,586, filed on Mar. 5, 2014, now Pat. No. 9,651,142.
(Continued)

(51) Int. Cl.
*G01K 1/02* (2006.01)
*G01K 1/14* (2006.01)
(Continued)

(52) U.S. Cl.
CPC ......... *F16H 57/01* (2013.01); *F16H 57/0405* (2013.01); *G01N 25/72* (2013.01); *H05K 7/20854* (2013.01)

(58) Field of Classification Search
CPC .. F16H 59/72; F16H 61/0006; F16H 57/0405; F16H 48/00; F16H 48/18;
(Continued)

(56) References Cited

U.S. PATENT DOCUMENTS 3,548,683 A * 12/1970 Fisher ................... F16H 48/147
475/164
3,550,724 A * 12/1970 Vollmer .............. F16H 57/0421
184/11.1
(Continued)

FOREIGN PATENT DOCUMENTS

DE 10016640 C1 9/2001
EP 1508915 A2 2/2005
(Continued)

OTHER PUBLICATIONS

International Search Report with Written Opinion, PCT/US2014/021547, dated Jun. 12, 2014.
(Continued)

*Primary Examiner* — Gail Kaplan Verbitsky
(74) *Attorney, Agent, or Firm* — Marshall & Melhorn, LLC

(57) ABSTRACT

A method of sensing an internal temperature of a differential carrier includes providing a differential carrier temperature sensing package with an electronic circuit board having a first temperature sensor that is in thermally conductive contact with a thermal conductor, where the thermal resistance of the package and thermal conductor is given and known as $R_{ENC}$. The package is extended through an opening in a differential carrier that has a fluid in it. The first temperature sensor senses a differential fluid temperature $T_{SNS}$. The electronic circuit board further has a second temperature sensor, whereby the thermal resistance of the circuit board is a given known resistance $R_{PCB}$. The second temperature sensor senses an internal package temperature $T_{PCB}$ within the package. Consequently, an internal temperature of the differential is calculated from the equation:

$$T_{INT} = T_{SNS}(1 + R_{ENC}/R_{PCB}) - T_{PCB}(R_{ENC}/R_{PCB}).$$

8 Claims, 2 Drawing Sheets

Related U.S. Application Data

(60) Provisional application No. 61/775,929, filed on Mar. 11, 2013, provisional application No. 61/775,959, filed on Mar. 11, 2013.

(51) Int. Cl.

| | | |
|---|---|---|
| *F16H 48/18* | (2006.01) | |
| *F16H 61/00* | (2006.01) | |
| *F16H 57/01* | (2012.01) | |
| *F16H 57/04* | (2010.01) | |
| *G01N 25/72* | (2006.01) | |
| *H05K 7/20* | (2006.01) | |

(58) Field of Classification Search
CPC ...... F16H 61/00; F16H 57/043; F16H 57/033; F16H 57/0434; F16H 57/0469; F01M 5/001; F01M 5/002; F01M 5/005; G01K 25/72; G01K 7/01; G01K 7/02; G01K 7/425; G01K 1/14; G01K 1/16; G01K 2217/00; H05K 7/20854; Y10T 74/19991; Y10T 29/49465; Y10T 74/2186
USPC ....... 374/144, 145, 147, 148, 208, 137, 153; 475/220, 230
See application file for complete search history.

(56) References Cited

U.S. PATENT DOCUMENTS

| | | | | |
|---|---|---|---|---|
| 5,033,575 A | * | 7/1991 | Takeshita | B60K 23/0808 180/233 |
| 5,076,708 A | * | 12/1991 | Pierson | F16H 57/0413 123/196 AB |
| 6,092,926 A | | 7/2000 | Still et al. | |
| 6,186,277 B1 | * | 2/2001 | Tervo | F16H 57/0482 184/11.1 |
| 7,077,463 B2 | | 7/2006 | Xiao et al. | |
| 7,698,090 B2 | | 4/2010 | Lima | |
| 7,980,983 B2 | * | 7/2011 | Schrand | F16H 48/08 475/160 |
| 8,248,800 B2 | | 8/2012 | Takata et al. | |
| 8,746,966 B2 | | 6/2014 | Kerkhof et al. | |
| 9,022,158 B2 | | 5/2015 | Mita | |
| 9,182,262 B2 | | 11/2015 | Wiest et al. | |
| 9,334,950 B2 | * | 5/2016 | Paielli | G01N 25/72 |
| 9,651,142 B2 | * | 5/2017 | Paielli | F16H 61/0006 |
| 2006/0054411 A1 | | 3/2006 | Fett et al. | |
| 2009/0215575 A1 | * | 8/2009 | Schrand | F16H 48/08 475/231 |
| 2015/0308293 A1 | | 10/2015 | Huntington et al. | |
| 2015/0369354 A1 | * | 12/2015 | Chudy | F16H 57/0483 165/41 |

FOREIGN PATENT DOCUMENTS

| | | | | |
|---|---|---|---|---|
| EP | 1637849 A1 | | 3/2006 | |
| EP | 2482050 A2 | | 8/2012 | |
| JP | 07208589 A | * | 8/1995 | .......... F16C 33/6659 |
| JP | 10103454 A | * | 4/1998 | .......... F16C 33/6674 |
| JP | 11182655 A | * | 7/1999 | .......... F16H 57/0421 |
| JP | 2005344863 A | * | 12/2005 | .......... F16H 57/0413 |
| JP | 2016138575 A | * | 8/2016 | |
| WO | 9928149 A1 | | 6/1999 | |
| WO | 2012074112 A1 | | 6/2012 | |

OTHER PUBLICATIONS

International Search Report with Written Opinion, PCT/US2014/021519, dated Sep. 17, 2014.
Machine-generated English Translation of DE10016640, obtained via Espacenet Patent Search.
Machine-generated English Translation of WO2012074112, obtained via Espacenet Patent Search.

* cited by examiner

DIFFERENTIAL CARRIER TEMPERATURE SENSING METHOD

RELATED APPLICATION

This application claims the benefit under 35 U.S.C. § 119(e) of U.S. Provisional Patent Application Ser. Nos. 61/775,929 and 61/775,959, both of which were filed on Mar. 11, 2013, and is a divisional application of U.S. patent application Ser. No. 14/197,586, that was filed Mar. 5, 2014 under 35 U.S.C. § 111(b), which applications are incorporated by reference herein in their entirety.

FIELD OF THE INVENTION

The present invention relates to a temperature sensing method for the inside of a vehicle differential.

BACKGROUND OF THE INVENTION

A vehicle differential is a device employing differential gears within a housing called a differential carrier. The vehicle differential is connected to three shafts. An input shaft transmits torque and rotation from a vehicle engine into the differential gears. In turn, each of the other two shafts separately transmits a portion of the torque and rotation from the differential gears out to separate external wheels.

For lubrication of the meshing of the differential gears, the differential gears within the differential carrier are at least partially submerged in a lubricant, for example, a mineral—standard base lubricant or a synthetic—premium lubricant. In either case, the lubricant may be certified as an API GL5 classification oil or SAE J2360 standard oil, and sealed within the differential carrier housing.

As a result of initial machining of the differential and associated parts therein, along with rigorous meshing of the differential gears during the differential's operation over an extended period of time, metal particles enter the lubricant within the differential and cause friction within. In turn, the friction affects the thermal conditions by increasing the temperature within the differential, which in turn causes more wear on the associated parts.

In general, when the rear wheels of a vehicle are caused to turn or are experiencing wheel slippage, as quite often happens, an outside wheel(s) makes a larger radius than an inside wheel(s). As a result, the outside wheel goes a farther distance, moves faster, and turns more revolutions than the inside wheel. Consequently, when both wheels are on the same axle shaft, one or both wheels would have to skid or slip to make a turn. However, by applying a differential between the rear wheels, the wheels are allowed to turn at different speeds.

As a vehicle operates, the meshing and rotation of differential gears, along with the presence of metal particles in the oil of the differential, friction increases. This results in heat building up within the space, oil, and parts that comprise the differential. Consequently, the differential experiences temperature swings and potentially high operational temperatures that can lead to part failures. Hence, it would advantageous to know the thermal conditions within the differential carrier, in order to detect potential part failures and long term reliability problems.

Currently, due to high costs, there is a lack of sealing means and durability requirements for sensing temperature within the harsh environment of the differential. This is compounded by the use of slow responding sensors that are disposed directly in the differential, in order to measure conditions therein. Unfortunately, current practices result in reducing or even eliminating the effectiveness of early detection of failures within a differential.

Consequently, it would be beneficial to provide a method for temperature sensing within a differential carrier that would be based on direct and current conditions therein. This would result in a more accurate and reliable monitoring of the differential. In turn, such a method would result in a better operation of a vehicle and a better quality differential that is more reliable.

SUMMARY OF THE INVENTION

A differential carrier temperature sensing package is used to determine the internal temperature $T_{INT}$ of a differential carrier by utilizing a sensed differential fluid temperature $T_{SNS}$, an internal package temperature $T_{PCB}$, a thermal resistance of the package plus a thermal conductor $R_{ENC}$, and a thermal resistance at an electronic circuit board $R_{PCB}$ within the package. As a result, an accurate and quick determination of an internal temperature of a differential carrier is made.

In a first embodiment, a differential carrier temperature sensing package comprises a differential package housing that comprises an upper portion and a lower portion that are sealed together. The two package portions may be unitary. The upper portion and the lower portion are in thermal contact with an environment that is external to a differential carrier housing. The lower portion is also in thermally conductive contact with an outer surface of the differential carrier housing, where the lower portion of the differential package housing extends through an opening in the differential housing, thereby being in thermally conductive contact with a fluid within the differential housing. The fluid may be in a form of a liquid and/or vapor.

The package housing further comprises an electronic circuit, and first and second temperature sensors. The electronic circuit is attached to the upper portion within the package housing and is in thermally conductive contact with the upper portion. The first temperature sensor is disposed on the electronic circuit and is in thermally conductive contact with a thermal conductor that is disposed within the package housing. The thermal conductor is imbedded in, and consequently, is in thermally conductive contact with the lower portion, which in turn is in thermally conductive contact with the fluid within the differential housing. The differential fluid temperature $T_{SNS}$ is determined by thermal conduction through the electronic circuit, the first sensor, the thermally conductive conductor, and the lower portion of the package housing.

The second temperature sensor is disposed on the electronic circuit. The temperature at the electronic board $T_{PCB}$, which is taken to be the temperature within the package housing, is determined by thermal conduction from the electronic circuit tp the second sensor. Hence, with a given known thermal resistance $R_{ENC}$ of the combination of the package housing and the thermal conductor, along with a given known thermal resistance $R_{PCB}$ of the electronic circuit board (i.e., not in contact with the thermal conductor), the electronic circuit can determine an internal carrier temperature $T_{INT}$, which can be communicated outside of the package housing, for monitoring and controlling a vehicle within which the differential carrier resides.

In a second embodiment, a differential carrier temperature sensing package comprises a package housing that comprises an upper portion and a lower portion that are sealed together. The two package housing portions may be unitary. The upper portion and the lower portion are in thermal contact with an environment that is external to a differential carrier housing. The lower portion is also in thermally conductive contact with an outer surface of the differential housing, where the lower portion of the package housing extends through an opening in the differential housing, thereby being in thermally conductive contact with a fluid within the differential housing. The fluid may be in a form of a liquid and/or vapor.

The package housing further comprises an electronic circuit, and first and second temperature sensors. The electronic circuit is attached to and is in thermally conductive contact with the upper portion within the package housing. The first temperature sensor is disposed on the electronic circuit and is in thermally conductive contact with an outward projection of the lower portion, which in turn is in thermally conductive contact with a thermally conductive conductor. In contrast to the thermally conductive conductor of the first embodiment, here the thermal conductor is disposed in the fluid that is within the differential housing, with the outward projection surrounding the thermally conductive conductor. Further, the thermal conductor may have a lower thermal conductor portion that has a larger surface area than the upper portion, so as to make it more capable of quickly responding to thermal changes within the fluid. Hence, by way of the electronic circuit, the first sensor, outward projection of the lower portion, thermal conductor, and possibly the lower thermal conductor portion, the differential fluid temperature $T_{SNS}$ is determined.

The second temperature sensor is disposed on the electronic circuit for sensing the temperature within the package housing (i.e., not in contact with the thermal conductor). The temperature at the electronic board $T_{PCB}$ is determined by way of the electronic circuit and the second sensor. Hence, with a known thermal resistance $R_{ENC}$ of the combination of the package housing, the thermal conductor, and possibly the lower thermal conductor, and a known thermal resistance $R_{PCB}$ of the electronic circuit board, then the electronic circuit can determine an internal carrier temperature $T_{INT}$. This internal carrier temperature $T_{INT}$ can be communicated outside of the package housing for monitoring and controlling a vehicle within which the differential carrier resides.

Hence, the internal carrier temperature $T_{INT}$ can be determined based on the below-stated equation 2 using the below-found temperatures $T_{SNS}$ and $T_{PCB}$, for this embodiment, along with the given known $R_{ENC}$ and $R_{PCB}$.

Further objects and advantages of the present invention will be apparent from the following description and appended claims, reference being made to the accompanying drawings forming a part of a specification, wherein like reference characters designate corresponding parts of several views.

DESCRIPTION OF THE INVENTION

It is to be understood that the invention may assume various alternative orientations and step sequences, except where expressly specified to the contrary. It is also to be understood that the specific devices and processes illustrated in the attached drawings, and described in the following specification are simply exemplary embodiments of the inventive concepts defined in the appended claims. Hence, specific dimensions, directions or other physical characteristics relating to the embodiments disclosed are not to be considered as limiting, unless the claims expressly state otherwise.

Figure 1:
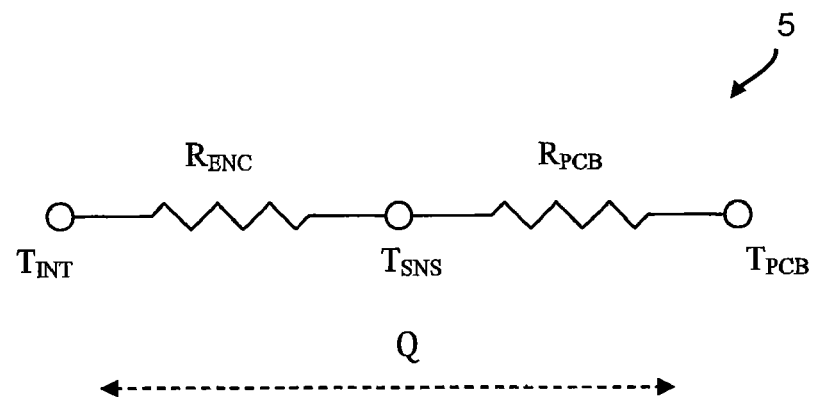
FIG. 1 is a first thermal circuit schematic diagram in accordance with the present invention.

FIG. 1 illustrates a simplified thermal circuit schematic diagram of an internal differential carrier temperature $T_{INT}$ that is determined by utilizing a measured differential carrier fluid temperature $T_{SNS}$ and an internal housing package temperature $T_{PCB}$, in combination with a given known thermally conductive resistance $R_{ENC}$ of a housing and a thermal conductor, and a given known thermal resistance $R_{PCB}$ of the housing at an electronic circuit board.

Specifically in FIG. 1, the thermal energy Q flows through circuit 5 in a direction that is determined by the temperatures of the inside and outside of a differential carrier. When the inside temperature is higher than the outside temperature, thermal energy flows from $T_{INT}$ to $T_{PCB}$, because the temperature at the point of the $T_{PCB}$ is close to that on the outside of the differential carrier. However, when the outside temperature is higher than the inside temperature, thermal energy flows from the outside temperature point $T_{PCB}$ to $T_{INT}$ within the differential carrier. The following equation 1 expresses the circuit thermal flow.

$$Q=(T_{INT}-T_{SNS})/R_{ENC}=(T_{SNS}-T_{PCB})/R_{PCB} \quad (eq.\ 1)$$

Consequently, solving for $T_{INT}$ within equation 1 results in equation 2 for determining the internal carrier temperature.

$$T_{INT}=T_{SNS}(1+R_{ENC}/R_{PCB})-T_{PCB}(R_{ENC}/R_{PCB}) \quad (eq.\ 2)$$

Figure 3:
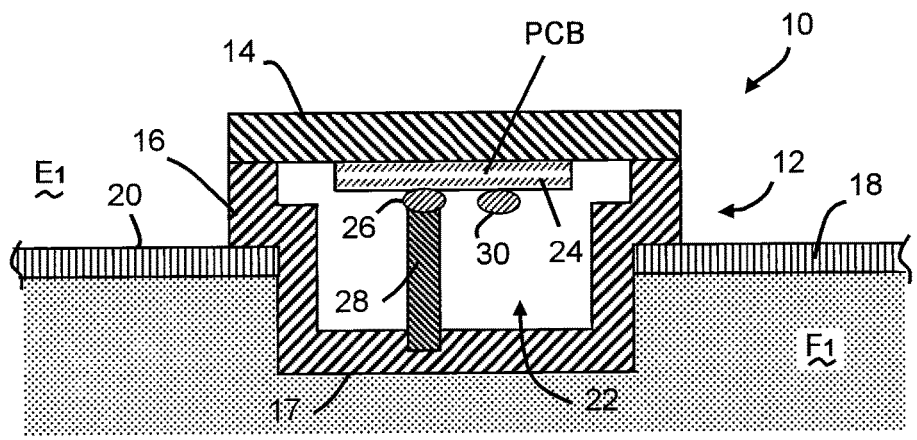
FIG. 3 is a cross sectional view of a first differential carrier temperature sensing package in accordance with the present invention.

FIG. 3 illustrates a first embodiment of a differential carrier temperature sensing package 10 having a package housing 12 that comprises an upper portion 14 and a lower portion 16 that are sealed together. The two package portions 14, 16 may be unitary. The upper portion 14 comprises very conductive thermal material, for example, a thermally conductive metal like aluminum. The lower portion 16 comprises a significantly less thermally conductive material than that of the upper portion 14, for example, a high temperature plastic. Both portions 14, 16 are in thermally conductive contact with an environment $E_1$ that is external to a differential carrier housing 18. The lower portion 16 is also in thermally conductive contact with an outer surface 20 of the differential housing 18, where the lower portion 16 of the package housing 12 extends through an opening 22 in the differential housing 18, thereby allowing the lower portion 16 to be in thermally conductive contact with a fluid $F_1$ within the differential housing 18. The fluid $F_1$ may be in a form of a liquid and/or vapor.

The package housing 12 further comprises an electronic circuit 24 with first and second temperature sensors 26, 30 disposed thereon. The electronic circuit 24 is in close thermally conductive contact with the first and second temperature sensors 26, 30 that preferably are common negative temperature coefficient (NTC) thermistors. The electronic circuit 24 is also in thermally conductive contact with and attached to the upper portion 14 within the package housing 12.

The first temperature sensor 26 is also in close thermally conductive contact with a thermal conductor 28, which may be a simple aluminum rod that is disposed within the package housing 12. The thermal conductor 28 is imbedded in and consequently in thermally conductive contact with the lower portion 16 but not in contact with the outer surface 17 of the lower portion 16. The lower portion 16 is in thermally conductive contact with the fluid $F_1$ within the differential housing 18. The differential fluid temperature $T_{SNS}$ is determined by way the thermal conduction between the electronic circuit 24, the first sensor 26, the thermal conductor 28, and the lower portion 16 of the package housing 12.

The second temperature sensor 30 is disposed on the electronic circuit 24. The temperature $T_{PCB}$ at the electronic circuit 24 is determined by the electronic circuit 24 sensing the second sensor 30. Hence, with a given known thermal resistance $R_{ENC}$ of the combination of the package housing 12 and the thermal conductor 28, along with a given known thermal resistance $R_{PCB}$ of the electronic circuit board PCB, the electronic circuit 24, wherein the electronic circuit 24 is disposed on the electronic circuit board PCB, can determine an internal carrier temperature $T_{INT}$. Then, the temperature $T_{INT}$ can be communicated outside of the package housing 12 for monitoring and controlling a vehicle within which the differential carrier sensing package 10 is installed.

Figure 4:
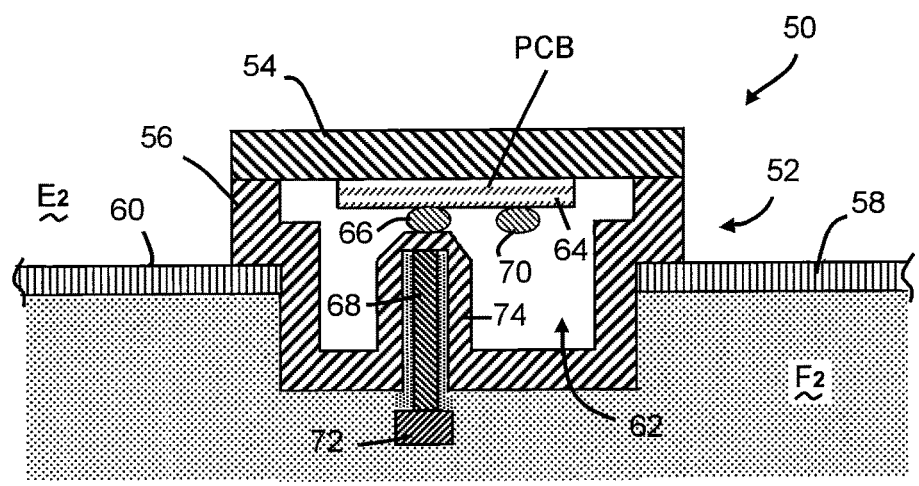
FIG. 4 is a cross sectional view of a second differential carrier temperature sensing package in accordance with the present invention.

In a second embodiment, which is depicted in FIG. 4, a differential carrier temperature sensing package 50 comprises a package housing 52 that comprises an upper portion 54 and a lower portion 56 that are sealed together. The two package housing portions 54, 56 may be unitary. The upper portion 54 and the lower portion 56 are in thermally conductive contact with an environment $E_2$ that is external to a differential carrier housing 58. The lower portion 56 is also in thermally conductive contact with an outer surface 60 of the differential housing 58, where the lower portion 56 of the package housing 52 extends through an opening 62 in the differential housing 58, thereby being in thermally conductive contact with a fluid $F_2$ within the differential housing 58. The fluid $F_2$ may be in a form of a liquid and/or vapor.

The package housing 52 further comprises an electronic circuit 64, and first and second temperature sensors 66, 70. The electronic circuit 64 is attached to the upper portion 54 within the package housing 52 and is in thermally conductive contact therewith. The first temperature sensor 66 is disposed on the electronic circuit 64 and is in thermally conductive contact with an outward projection 74 of the lower portion 56, which in turn is in thermally conductive contact with a thermal conductor 68. In contrast to the thermal conductor 28 of the first embodiment, the thermal conductor 68 is disposed in the fluid $F_2$ that is within the differential housing 58, with the outward projection 74 surrounding the thermal conductor 68 and with fluid $F_2$ therebetween. Further, the thermal conductor 68 may have an inward thermal conductor portion 72 that has a larger surface area than the upper thermal conductor 68, so as to make it more capable of quickly responding to thermal changes within the fluid $F_2$. Hence, the differential fluid temperature $T_{SNS}$ is determined by way of thermal conduction between the electronic circuit 64, the first sensor 66, outward projection 74 of the lower portion 56, thermal conductor 68, and possibly the inward thermal conductor portion 72.

The second temperature sensor 70 is disposed on the electronic circuit 64 for sensing the temperature within the package housing 52. The temperature at the electronic board $T_{PCB}$ is determined by way of the electronic circuit 64 and the second sensor 70. Hence, with a known thermal resistance $R_{ENC}$ of the combination of the package housing 52, the thermal conductor 68 with possibly the inward thermal conductor 72, and a known thermal resistance $R_{PCB}$ of the electronic circuit board 64, then the electronic circuit 64 can determine an internal carrier temperature $T_{INT}$. Thus, $T_{INT}$ can be communicated outside of the package housing 52 for monitoring and controlling a vehicle within which the differential carrier 50 resides, by the electronic control circuit 64.

Hence, the internal carrier temperature $T_{INT}$ can be determined based on the above-stated equation (eq. 2), while using the above-found temperatures $T_{SNS}$ and $T_{PCB}$, for this embodiment, along with the known $R_{ENC}$ and $R_{PCB}$.

The above-stated models that are described by equations (1) and (2), and illustrated in FIGS. 1, 3, and 4, result in accurate determinations of live temperature conditions within the differential carriers 10 and 50. These models are significantly faster at determining temperatures within a differential carrier than prior art systems. Consequently, the above-stated embodiments are significantly better than prior art at monitoring internal differential temperatures. In turn, these beneficial means should result in a better operation of a vehicle and a better quality differential carrier that is more reliable.

Figure 2:
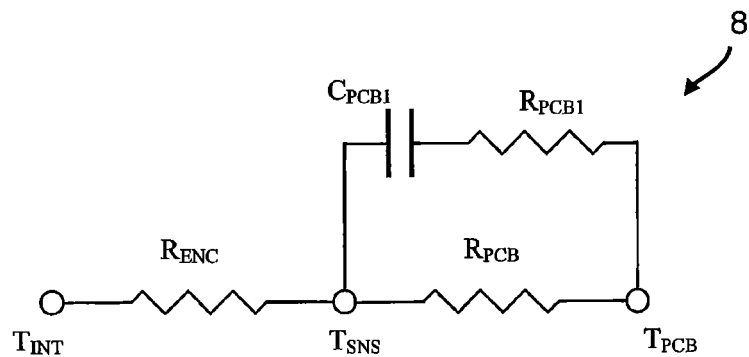
FIG. 2 is a second thermal circuit schematic diagram in accordance with the present invention.

Further, FIG. 2 illustrates a more accurate thermal schematic diagram for deriving an internal differential carrier temperature. This model provides for an expression of the dynamic behavior of the thermal circuit 8, which modifies FIG. 1 by adding the components $C_{PCB1}$, $R_{PCB1}$ in parallel with $R_{PCB}$ so as to result in a base $R'_{PCB}$ that more closely matches the thermal operation of the differential carriers 10, 60. This model results in the following equation 3:

$$Q = (T_{INT} - T_{SNS})/R_{ENC} = (T_{SNS} - T_{PCB})/R'_{PCB} \quad \text{(eq. 3)}$$

where $R'_{PCB}$ is equal to:

$$R'_{PCB} = \frac{R_{PCB}(sR_{PCB1}C_{PCB1} + 1)}{sC_{PCB1}(R_{PCB} + R_{PCB1}) + 1} \quad \text{(eq. 4)}$$

The factor "s" is defined to be a Laplace complex argument. The capacitance $C_{PCB1}$ in this dynamic model equation provides for the description of the rate of thermal flow in the assembly. This rate can be used to provide predictive information thereby functioning to effectively increase the response time of an internal differential carrier temperature measurement.

In accordance with the provisions of the patent statutes, the principles and modes of operation of this invention have been described and illustrated in its preferred embodiments. However, it must be understood that the invention may be practiced otherwise than specifically explained and illustrated without departing from its spirit or scope.

What is claimed is:

1. A method of determining an internal differential carrier temperature $T_{INT}$, comprising:
    measuring a temperature $T_{SNS}$ of a fluid within a differential carrier;
    measuring an internal temperature $T_{PCB}$ of an electronic circuit board disposed within a package housing of a temperature sensing package;
    utilizing a known housing plus thermal conductor thermal resistance $R_{ENC}$ of a thermal conductor disposed within the package housing; and
    utilizing a known thermal conductor resistance of the package housing at the electronic circuit board $R_{PCB}$ disposed within the package housing of the temperature sensing package, wherein an internal differential carrier temperature $T_{INT}$ is calculated by way of the equation: $T_{INT}=T_{SNS}(1+R_{ENC}/R_{PCB})-T_{PCB}(R_{ENC}/R_{PCB})$ wherein the internal differential carrier temperature Tint is to be used to monitor and control a vehicle within which the differential carrier resides.

2. The method of determining an internal differential carrier temperature of claim 1, wherein thermal energy is conducted from the interior of the differential carrier to the electronic circuit board of the temperature sensing package when the temperature inside the differential carrier is higher than the temperature outside the differential carrier.

3. The method of determining an internal differential carrier temperature of claim 1, wherein thermal energy is conducted from the electronic circuit board of the temperature sensing package to the interior of the differential carrier when the temperature outside the differential carrier is higher than the temperature inside the differential carrier.

4. A method of determining an internal differential carrier temperature, comprising:
providing a package housing comprising an upper portion and a lower portion connected together to form a sealed package housing, wherein the upper portion and the lower portion are in thermally conductive contact with an environment external to a differential carrier housing, wherein the lower portion is in thermally conductive contact with an outer surface of the differential carrier housing, wherein the lower portion of the package housing extends through an opening in the differential carrier housing, and wherein the lower portion of the package housing is in thermally conductive contact with a fluid within the differential carrier housing;
providing an electronic circuit attached to the upper portion within the package housing, and wherein the electronic circuit is in thermally conductive contact with the upper portion of the package housing;
providing a first temperature sensor disposed on the electronic circuit and in thermally conductive contact with a thermal conductor imbedded in and in thermally conductive contact with the lower portion of the package housing, wherein the lower portion of the package housing is in thermally conductive contact with the fluid within the differential carrier housing;
providing a second temperature sensor disposed on the electronic circuit;
measuring a temperature $T_{SNS}$ of the fluid within the differential carrier and an internal temperature $T_{PCB}$ of the electronic circuit board disposed within the package housing; and
utilizing a known package housing plus thermal conductor thermal resistance $R_{ENC}$ of the thermal conductor disposed within the package housing, and a known thermal conductor resistance of the package housing at the electronic circuit board $R_{PCB}$, wherein an internal differential carrier temperature $T_{INT}$ is determined by way of the equation $T_{INT}=T_{SNS}(1-R_{ENC}/R_{PCB})-T_{PCB}(R_{ENC}/R_{PCB})$ wherein the internal differential carrier temperature Tint is to be used to monitor and control a vehicle within which the differential carrier resides.

5. A method of determining an internal differential carrier temperature, comprising:
providing a package housing comprising an upper portion and a lower portion connected together to form a sealed package housing, wherein the upper portion and the lower portion are in thermally conductive contact with an environment external to a differential carrier housing, wherein the lower portion of the package housing is in thermally conductive contact with an outer surface of the differential carrier housing, wherein the lower portion of the package housing is extends through an opening in the differential carrier housing, and wherein the lower portion of the package housing is in thermally conductive contact with a fluid within the differential carrier housing;
providing an electronic circuit attached to the upper portion of the package housing within the package housing, and wherein the electronic circuit is in thermally conductive contact with the upper portion of the package housing;
providing a thermal conductor imbedded in and in thermally conductive contact with the lower portion of the package housing, and wherein the lower portion of the package housing is in thermally conductive contact with the fluid within the differential carrier housing;
measuring a temperature $T_{SNS}$ of the fluid within the differential carrier and an internal temperature $T_{PCB}$ of an electronic circuit board disposed within the package housing; and
utilizing a known package housing plus thermal conductor thermal resistance $R_{ENC}$ of the thermal conductor disposed within the package housing, and a known thermal conductor resistance of the package housing at the electronic circuit board $R_{PCB}$, wherein an internal differential carrier temperature $T_{INT}$ is determined by way of the equation $T_{INT}=T_{SNS}(1+R_{ENC}/R_{PCB})-T_{PCB}(R_{ENC}/R_{PCB})$ wherein the internal differential carrier temperature Tint is to be used to monitor and control a vehicle within which the differential carrier resides.

6. The method of determining an internal differential carrier temperature of claim 5, wherein thermal energy is conducted from the interior of the differential carrier to the electronic circuit board of the temperature sensing package when the temperature inside the differential carrier is higher than the temperature outside the differential carrier.

7. The method of determining an internal differential carrier temperature of claim 5, wherein thermal energy is conducted from the electronic circuit board of the temperature sensing package to the interior of the differential carrier when the temperature outside the differential carrier is higher than the temperature inside the differential carrier.

8. A method of determining an internal differential carrier temperature $T_{INT}$, comprising:
measuring a temperature $T_{SNS}$ of a fluid within a differential carrier;
measuring an internal temperature $T_{PCB}$ of an electronic circuit board disposed within a package housing of a temperature sensing package;
utilizing a known housing plus thermal conductor thermal resistance $R_{ENC}$ of a thermal conductor disposed within the package housing;
utilizing a known thermal conductor resistance of the package housing at an electronic circuit board $R_{PCB}$ disposed within the package housing of the temperature sensing package; and
utilizing a known series dynamic thermal capacitance $C_{PCB1}$ and dynamic thermal resistance $R_{PCB1}$ of the package housing at an electronic circuit board disposed within the package housing of the temperature sensing package, wherein the electronic circuit board is in parallel with the base $R_{PCB}$, wherein an internal differential carrier temperature $T_{INT}$ is calculated by way of the equation: $T_{INT}=T_{SNS}(1+R_{ENC}/R_{PCB})-T_{PCB}(R_{ENC}/R'_{PCB})$, wherein $R'_{PCB}=(R_{PCB}(sR_{PCB1} \cdot C_{PCB1}+$ 1))/(s$C_{PCB1}$($R_{PCB}$+$R_{PCB}$1+1)) wherein the internal differential carrier temperature Tint is to be used to monitor and control a vehicle within which the differential carrier resides.

* * * * *